United States Patent [19]

McNally

[11] 4,313,907
[45] Feb. 2, 1982

[54] APPARATUS FOR THE DETECTION OF A COMBUSTIBLE GAS

[75] Inventor: Frank X. McNally, Venetia, Pa.

[73] Assignee: National Mine Corporation, Pittsburgh, Pa.

[21] Appl. No.: 142,025

[22] Filed: Apr. 21, 1980

[51] Int. Cl.³ .............................................. G01N 27/16
[52] U.S. Cl. ........................................ 422/97; 338/34; 422/96
[58] Field of Search ....................... 422/96, 94, 97, 98; 23/232 E; 73/27 R; 338/34; 340/633

[56] References Cited

U.S. PATENT DOCUMENTS

| | | | |
|---|---|---|---|
| 2,805,134 | 9/1957 | Strange | 422/97 |
| 2,904,406 | 9/1959 | Moore | 422/97 X |
| 3,200,011 | 8/1965 | Baker | 422/97 X |
| 4,045,177 | 8/1977 | McNally | 422/96 |
| 4,072,467 | 2/1978 | Jones | 422/97 |
| 4,193,964 | 3/1980 | John | 422/97 X |

Primary Examiner—Ronald Serwin
Attorney, Agent, or Firm—Stanley J. Price, Jr.; John M. Adams

[57] ABSTRACT

An improvement is provided in apparatus used to detect combustible gases, which embodies a Wheatstone bridge circuit including a refractory-coated detector element having thereon a catalyst for promoting oxidation of the combustible gas to be detected constituting one leg of the bridge and a refractory-coated reference element constituting a second leg of the bridge. The improvement, in its broadest aspect, consists in using a mixture of palladium, palladium oxide and nickel oxide as the catalyst on the detector element. In addition, an improved reference element is provided which has a coating of either sodium metasilicate or lead borate deposited thereon.

6 Claims, 1 Drawing Figure

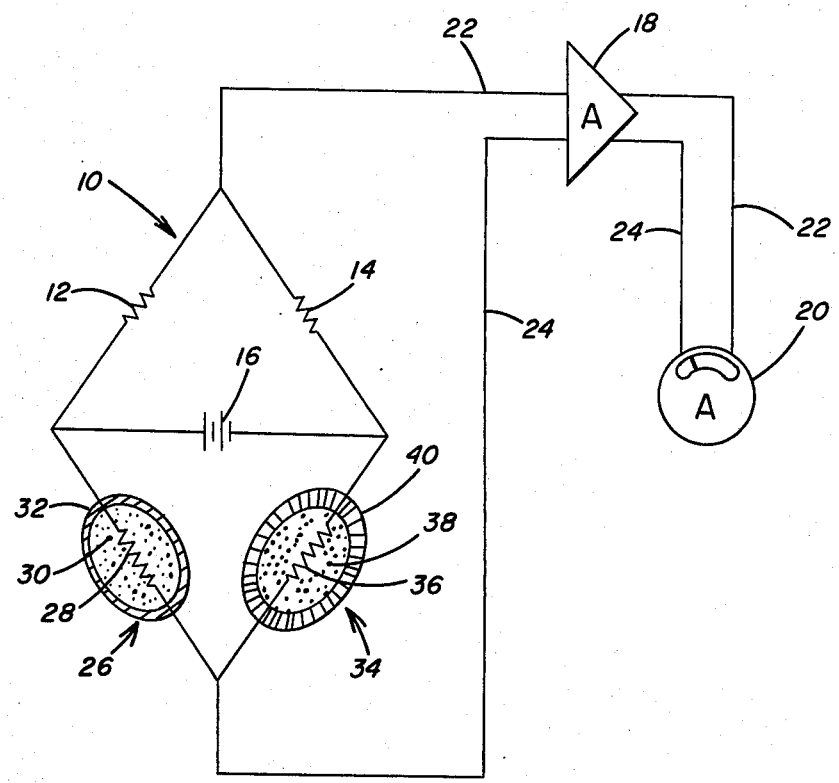

APPARATUS FOR THE DETECTION OF A COMBUSTIBLE GAS

This invention relates to an improvement in apparatus for detecting a combustible gas. The term "gas" as hereinafter used in the specification and claims means gas or vapor, or mixtures of gases and/or vapors.

Combustible gases are an ever-present threat to life and property in buildings or closed work areas. These gases include a myriad of different chemical compounds, for example aliphatic hydrocarbons such as methane, aromatic hydrocarbons such as benzene, alcohols such as methanol, esters such as butyl acetate, ethers such as ethylene oxide, and mixtures such as gasoline, etc.

In order to operate safely in confined areas where these gases are used, it is necessary to employ instrumentation for the detection of gases, and also to quantitatively measure the concentration of the gas. Infrared and flame ionization type instruments are often employed to detect the gases and measure their concentration. Such instruments are expensive, difficult to use, require skilled personnel, and further are subject to damage and require considerable maintenance.

An instrument which has been used successfully for detecting and measuring the concentration of combustible gases is a Wheatstone bridge circuit comprising two minute platinum coils as two legs of the bridge. Upon these coils is formed a refractory bead, and upon one bead is formed a catalytic coating. The latter is sometimes called a detector element; the former is sometimes called the reference element. When the detector element encounters a combustible gas and the Wheatstone bridge circuit is operated in the conventional manner, a signal is developed by the gas burning at the catalyst surface, heating the platinum coil and thereby generating the signal. Unfortunately, there are many shortcomings to the commercially available Wheatstone bridge instruments used to detect combustible gases. There is considerable difficulty in finding and forming a catalyst which will promote the reaction of the potentially large number of different chemicals with oxygen at the surface of the catalyst, thereby generating the warning signal. Further, the detector element, depending upon the composition of the catalyst, may respond to changes in the environment such as temperature or to changes in itself due to aging in a manner different from the response of the reference element, thus causing spurious signals to be generated.

In accordance with my invention, in its broadest aspect, I have provided an improved detector element for a Wheatstone bridge circuit which comprises a catalyst composed of palladium, palladium oxide, and nickel oxide. By virtue of the use of this catalyst, a signal is developed by the circuit upon encountering any combustible gas which is superior to the signal produced by present commercially available combustible detector elements.

The catalytic coating is applied to the refractory which envelopes the platinum coil by one or more successive treatments of the refractory, each treatment comprising the application of an aqueous solution of palladium chloride and nickel chloride to the refractory, passing a current through the platinum coil to thereby heat the element to a temperature and for a time in the presence of air such that the water is evaporated and a mixture of palladium, palladium oxide, and nickel oxide is formed as a coating on the refractory.

A further aspect of my invention is the use of an improved reference element in the Wheatstone bridge circuit. The improvement resides in the provision of a coating on the refractory of the reference element which contains either a sodium metasilicate glass, or a lead borate glass. Either of these coatings operates in concert with and complements the physical characteristics of the catalyst of the detector element so that spurious signals do not result.

The sodium metasilicate coating is formed by dissolving the metasilicate in water, applying the solution to the refractory of the reference element, and heating the element to drive off the water and form a glassy coating composed of the silicate. Repeated applications of the solution may be required to form a coating of the requisite thickness to effectively complement the detector element. The lead borate coating is similarly formed, starting with an aqueous solution of lead nitrate and boric acid which interact to form lead borate in the aqueous solution. Evaporation of the water followed by further heating at elevated temperature results in the formation of a lead borate glassy coating on the refractory.

For a better understanding of my invention, its objects and advantages, reference should be had to the following description of the preferred embodiment and to the accompanying drawing which is a schematic showing of the preferred embodiment.

Referring to the drawing there is shown a Wheatstone bridge circuit generally designated by the numeral 10. The circuit has two fixed resistors 12 and 14 and a source of potential 16. The output from the circuit is connected through an amplifier 18 to an analogue meter 20 via conductors 22 and 24. The circuit includes a gas detector element designated generally by the numeral 26. This detector element comprises a platinum resistor coil 28 which has an alumina ($Al_2O_3$) refractory coating 30 over which is coated a catalyst for gas oxidation designated by the numeral 32. The catalyst is a mixture of palladium, palladium oxide and nickel oxide which is deposited on the alumina refractory in the manner generally described above and more specifically described later in the Experimental Section. The circuit also includes a reference element designated generally by the numeral 34. The reference element comprises a platinum resistor coil 36 coated with an alumina refractory layer 38 over which is deposited a glassy coating 40 of lead borate as previously described, and later more specifically described in the Experimental Section.

The operation of the bridge circuit is as follows. By suitable selection of resistors there is a zero output from the bridge circuit in the absence of a combustible gas at the detector element 26. In the presence of a combustible gas, the gas is oxidized at the element 26. The oxidation is promoted by the catalyst 32. Since the oxidation is an exothermic reaction, the temperature of the detector element and, accordingly, of the platinum coil 28 is increased. The temperature of the platinum coil 36 of the reference element 34, however, remains unaffected as there is no oxidation of the combustible gas at this element. As the temperature of the detector element 26 increases, relative to the reference element 34, the resistance of coil 28 correspondingly increases relative to the resistance of the coil 36 of the reference element 34. Consequently, the bridge becomes unbalanced, and a signal is produced via the conductors 22 and 24 to amplifier 18. This signal is approximately proportional to the increase in resistance of the detector element 26 and accordingly to the oxidation of combustible gas as the detector, which in turn, is approximately proportional to the amount or concentration of combustible gas in the atmosphere at the detector element. The signal is amplified by the amplifier 18, and transmitted to the analogue ammeter 20 which is suitably calibrated to provide a readout proportional to the combustible gas in the atmosphere.

EXPERIMENTAL SECTION

The following five experiments are reported to illustrate my invention and to compare the results of the use of my invention with the results obtained from Wheatstone bridge circuits not using my invention. Experiments 1 and 2 are the ones reported solely for comparison purposes while Experiments 3, 4, and 5 are illustrative of the present invention. Results of the experiments are reported in the tables following the description of the experiments.

EXPERIMENT NO. 1

In this experiment a palladium catalyst was used in the detector element with no coating on the reference element. The formula of the parent composition for making the catalyst was as follows:

Palladium Chloride—$PdCl_2$—0.16 grams
Distilled Water—2 ml
Concentrated Acid—HCl—4.5 ml A small drop of the solution amounting to one microliter was applied to the alumina refractory of the detector element to form the catalyst. In order to heat the parent composition and produce the catalyst on the surface of the aluminum oxide refractory a current was passed through the platinum coil of the detector element. The following times and currents through the platinum coil have been found suitable:

| COAT # | CURRENT mA | TIME |
|---|---|---|
| 1 | 0 start to 400 finish | 1 min. |
| | Repeated 3 times, providing 4 coats. | |
| | +400 mA | 1 min. (no further catalyst addition) |

Reference—none

EXPERIMENT NO. 2

The catalyst for the detector element is identical to that used in Experiment No. 1. A cobalt oxide coating was formed on the alumina refractory of the reference element. The parent composition for this coating had the following composition:

Cobalt Nitrate—$Co(NO_3)_2.6 H_2O$—0.582 grams
Distilled water—5 ml

One microliter of the parent solution was added to the alumina refractory of the reference element which was then heated by the passage of current through the platinum coil to dry and thermally convert the composition to cobalt oxides as follows:

| COAT # | CURRENT mA | TIME |
|---|---|---|
| 1 | 0–100 | 1 min. |
| | 100–200 | 1 min. |
| | 200–300 | 1 min. |
| | 300 | 1 min. |

Repeated 2 times, providing 3 coats.

EXPERIMENT NO. 3

In this experiment, a palladium—nickel catalyst of this invention was formed on the alumina refractory of the detector element. The formulation of the parent composition to form the catalyst on the detector element, was as follows:

Palladium Chloride—$Pd Cl_2$—0.080 grams
Nickel Chloride—$Ni Cl_2.6 H_2$—0.107 grams
Water—2 ml
Concentrated Acid—HCl ½ ml The salts were dissolved in the water, providing a catalyst with a ratio of palladium to nickel of one to one.

A small drop of the solution amounting to one microliter was then applied to the alumina refractory element to form the catalyst. In order to heat the parent composition and produce the catalyst on the surface of the aluminum oxide refractory, the following times and currents through the platinum coil were found suitable:

| COAT # | CURRENT mA | TIME |
|---|---|---|
| 1 | 0 start to 400 finish | 1 min. |

Repeated 3 times, providing 4 coats

A coating consisting of sodium metasilicate was applied to the alumina refractory of the reference element in the following manner: The parent composition of the coating was prepared from the following:

Sodium Metasilicate—$Na_2SiO_3.9 H_2O$—1.5 grams
Water—5 ml.

One microliter of this parent solution was then added to the alumina refractory of the reference element and heated to dryness and thermally converted to a glassy sodium silicate as follows:

| COAT # | CURRENT mA | TIME |
|---|---|---|
| 1 | 0–100 | 1 min. |
| | 100–200 | 1 min. |
| | 200–300 | 1 min. |
| | 300–350 | 1 min. |

Repeated 3 times, providing 4 coats

EXPERIMENT NO. 4

The catalyst used in the detector element was the same as that used in Experiment No. 3. A coating consisting of lead borate was applied to the reference element. The parent composition used to form the reference coating was made up as follows:

Lead Nitrate—$Pb (NO_3)_2$—0.331 grams
Distilled water 2.5 ml

A separate solution was made up as follows from:

Boric Acid—(ortho)—$H_3BO_3$—0.62 grams;
Distilled water 2.5 ml.

The two solutions were combined to make approximately 5 ml of a solution containing lead and Boron-oxygen ions in the approximate molar ratio of 1 to 1.

The reference coating was then applied to the reference element by adding one microliter of solution, heating to dryness, and thermally coverting the composition to a lead broate type glass as follows:

| COAT # | CURRENT mA | TIME |
|---|---|---|
| 1 | 0–100 | 1 min. |
|  | 100–200 | 1 min. |
|  | 200–300 | 1 min. |
|  | 350 | 1 min. |

Repeated once, providing 2 coats Additional treatment at 400 mA was given to the element for ½ minute. This treatment was followed by application of one more coat of solution in the manner of coat number one, thus providing a total of three coats.

EXPERIMENT NO. 5

A parent catalyst composition was prepared in the same manner as in Experiment No. 4 except that the nickel content was increased so that the resulting parent solution provided a ratio of palladium to nickel in the catalyst of one to two. The catalyst composition was then applied to the detector element in the same manner as in Experiment No. 4. A reference coating identical to that of Experiment No. 4, a lead borate glass, was applied to the reference element.

TABLE 1

| EXPERIMENT NO. | 1 | 2 | 3 | 4 | 5 |
|---|---|---|---|---|---|
| CATALYST COATING | Pd | Pd | Pd/Ni | Pd/Ni | Pd/2Ni |
| REFERENCE COATING | None | Co Ox | $Na_2SiO_3$ | $Pb_x(BO_2)_y$ | $Pb_x(BO_2)_y$ |
| GAS | SENSITIVITY - mV/% LEL* | | | | |
| methane | 1.39 | 1.05 | 1.27 | 1.35 | 1.29 |
| hexane | 0.30 | 0.11 | 0.72 | 0.85 | 0.88 |
| acetone | 0.26 | 0.05 | 0.85 | 0.95 | 1.06 |
| methanol | 0.46 | 0.08 | 1.16 | 1.04 | 1.30 |
| benzene | 0.16 | 0.12 | 0.51 | 0.65 | 0.67 |
| ethylene oxide | 0.25 | 0.09 | 1.08 | 1.28 | 1.37 |
| Average | 0.47 | 0.25 | 0.93 | 1.02 | 1.10 |
| Comparative Rating | 100% | 53% | 198% | 217% | 234% |

*Lower explosive limit

TABLE II

SUMMARY
Performance Characteristics

| Experiment No. | Catalyst Coating | Reference Coating | Performance Rating Averg. $\frac{mV}{\% LEL}$ | Temp. Coef. Zero Excur. at 0 C. | Comment |
|---|---|---|---|---|---|
| 1 | Pd | none | 0.47 (low) | 0.25% $CH_4$ 5% LEL | Entirely Unusable |
| 2 | Pd | CoOx | 0.25 (low) | 0% $CH_4$ 0% LEL | For methane, excellent For LEL, unusable |
| 3 | Pd/Ni | $Na_2SiO_3$ | 0.93 (high) | 0.10% $CH_4$ 2% LEL | For methane, poor For LEL, poor |
| 4 | Pd/Ni | $Pb_x(BO_2)_y$ | 1.02 (high) | 0% $CH_4$ 0% LEL | For methane, fair For LEL, good |
| 5 | Pd/2 Ni | $Pb_x(BO_2)_y$ | 1.10 (highest) | 0% $CH_4$ 0% LEL | For methane, good For LEL, excellent |

According to the provisions of the Patent Statutes, I have explained the principle, preferred construction and mode of operation of my invention and have illustrated and described what I now consider to represent its best embodiments. However, it should be understood that, within the scope of the appended claims, the invention may be practiced otherwise than as specifically illustrated and described.

I claim:

1. In an apparatus for detecting a combustible gas which comprises a Wheatstone bridge circuit having (a) a detector element comprising an electrically conducting member coated with a refractory and having on the surface of said refractory a catalyst for the oxidation of said gas, said detector element constituting one leg of said bridge, and (b) a reference element comprising an electrically conducting member coated with a refractory, said reference element constituting a second leg of said bridge, whereby upon catalytic oxidation of said gas an electrical signal approximately proportional to the amount of said gas present at the detector element is produced, the Improvement which comprises, a detector element having as said catalyst a composition containing palladium, palladium oxide and nickel oxide.

2. In an apparatus for detecting a combustible gas which comprises a Wheatstone bridge circuit having (a) a detector element comprising an electrically conducting member coated with a refractory and having on the surface of said refractory a catalyst for the oxidation of said gas, said detector element constituting one leg of said bridge, and (b) a reference element comprising an electrically conducting member coated with a refractory, said reference element constituting a second leg of said bridge, whereby upon catalytic oxidation of said gas an electrical signal approximately proportional to the amount of said gas present at the detector element is produced, the Improvement which comprises, a detector element having as said catalyst a composition containing palladium, palladium oxide and nickel oxide; and a reference element having a coating of a sodium metalsilicate glass deposited thereon.

3. In an apparatus for detecting a combustible gas which comprises a Wheatstone bridge circuit having (a) a detector element comprising an electrically conducting member coated with a refractory and having on the surface of said refractory a catalyst for the oxidation of said gas, said detector element constituting one leg of said bridge, and (b) a reference element comprising an electrically conducting member coated with a refractory, said reference element constituting a second leg of said bridge, whereby upon catalytic oxidation of said gas an electrical signal approximately proportional to the amount of said gas present at the detector element is produced, the Improvement which comprises, a detector element having as said catalyst a composition containing palladium, palladium oxide and nickel oxide; and a reference element having a coating of a lead borate glass deposited thereon.

4. A resistance element comprising a platinum coil coated with alumina on which is deposited a coating containing palladium, palladium oxide and nickel oxide.

5. A resistance element comprising a platinum coil coated with alumina on which is deposited a coating containing a sodium metasilicate glass.

6. A resistance element comprising a platinum coil coated with alumina on which is deposited a coating containing a lead borate glass.

* * * * *